(12) United States Patent
Vaddiraju et al.

(10) Patent No.: US 12,144,621 B2
(45) Date of Patent: Nov. 19, 2024

(54) MINIATURIZED ANALYTE SENSOR

(71) Applicant: Medtronic MiniMed, Inc., Northridge, CA (US)

(72) Inventors: Santhisagar Vaddiraju, Plymouth, MN (US); Shawn C. Kelley, Shoreview, MN (US)

(73) Assignee: MEDTRONIC MINIMED, INC., Northridge, CA (US)

(*) Notice: Subject to any disclaimer, the term of this patent is extended or adjusted under 35 U.S.C. 154(b) by 0 days.

(21) Appl. No.: 17/836,320

(22) Filed: Jun. 9, 2022

(65) Prior Publication Data

US 2022/0296131 A1  Sep. 22, 2022

Related U.S. Application Data (62) Division of application No. 16/194,073, filed on Nov. 16, 2018, now Pat. No. 11,382,541.

(51) Int. Cl.
| | |
|---|---|
| *A61B 5/1473* | (2006.01) |
| *A61B 5/00* | (2006.01) |
| *A61B 5/145* | (2006.01) |
| *A61B 5/1486* | (2006.01) |
| *A61B 5/1495* | (2006.01) |
| *G01N 33/49* | (2006.01) |

(52) U.S. Cl.
CPC .......... *A61B 5/1473* (2013.01); *A61B 5/0031* (2013.01); *A61B 5/14532* (2013.01); *A61B 5/1495* (2013.01); *G01N 33/49* (2013.01); *A61B 5/1486* (2013.01); *A61B 5/14865* (2013.01)

(58) Field of Classification Search
CPC . A61B 5/1473; A61B 5/0031; A61B 5/14532; A61B 5/1495; A61B 5/1486; A61B 5/14865; A61B 2560/063; G01N 33/49
See application file for complete search history.

(56) References Cited

U.S. PATENT DOCUMENTS

| | | | |
|---|---|---|---|
| 4,755,173 A | 7/1988 | Konopka et al. | |
| 5,243,516 A | 9/1993 | White | |
| 5,391,250 A | 2/1995 | Cheney, II et al. | |
| (Continued) | | | |

OTHER PUBLICATIONS

U.S Advisory Action dated Oct. 25, 2021 in U.S. Appl. No. 16/194,073.

(Continued)

*Primary Examiner* — Yi-Shan W. Yang
*Assistant Examiner* — Kyle W. Kretzer
(74) *Attorney, Agent, or Firm* — Weaver Austin Villeneuve & Sampson LLP (57) ABSTRACT

The disclosed techniques include applying, using a voltage controller, multiple voltage pulses to a working electrode of a two-electrode sensor probe, and measuring, using a current sensor, the current response to the applied multiple voltage pulses. The techniques also include analyzing, using a processor, the measured current response, and calibrating, using a processor, the current sensor on the basis of the analyzed measured current response. The techniques further include determining, using a processor, a glucose concentration value on the basis of the calibrated current sensor, and transmitting, using a transmitter, the determined glucose concentration value to a receiver.

12 Claims, 9 Drawing Sheets

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A * | 9/1998 | Gross .................. A61B 5/6848 600/347 |
| 5,807,375 A | 9/1998 | Gross et al. |
| 5,925,021 A | 7/1999 | Castellano et al. |
| 5,954,643 A | 9/1999 | Vanantwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,234,076 B2 | 7/2012 | Carpenter et al. |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 10,004,433 B2 | 6/2018 | Etzkorn |
| 10,739,350 B2 * | 8/2020 | Wu .................. G01N 27/3273 |
| 11,382,541 B2 | 7/2022 | Vaddiraju et al. |
| 2007/0123819 A1 | 5/2007 | Mernoe et al. |
| 2007/0299617 A1 * | 12/2007 | Willis .................. A61B 5/7225 204/403.01 |
| 2009/0194432 A1 * | 8/2009 | Deng .................. A61B 5/14532 205/792 |
| 2010/0160861 A1 | 6/2010 | Causey, III et al. |
| 2010/0185071 A1 * | 7/2010 | Simpson ................ C12Q 1/006 600/347 |

OTHER PUBLICATIONS

U.S. Final office Action dated Jul. 19, 2021 in U.S. Appl. No. 16/194,073.
U.S. Non-Final office Action dated Mar. 1, 2021 in U.S. Appl. No. 16/194,073.
U.S. Non-Final office Action dated Nov. 23, 2021 in U.S. Appl. No. 16/194,073.
U.S. Notice of Allowance dated Apr. 4, 2022 in U.S. Appl. No. 16/194,073.
U.S. Restriction Requirement dated Dec. 15, 2020 in U.S. Appl. No. 16/194,073.

* cited by examiner

MINIATURIZED ANALYTE SENSOR

CROSS-REFERENCE TO RELATED APPLICATIONS

The present application is a divisional of U.S. patent application Ser. No. 16/194,073, filed Nov. 16, 2018, which is hereby incorporated by reference herein in its entirety.

TECHNICAL FIELD

Embodiments of the subject matter described herein relate generally to sensors for measuring analyte concentrations.

BACKGROUND

Needle-implantable biosensors have shown to be useful for analyte monitoring applications, such as glucose monitoring applications for use in diabetes management.

Some needle-implantable glucose biosensors operate by monitoring the amount of $H_2O_2$ which is produced from the catalyzed reaction of glucose by $GO_x$, to gluconic acid and $H_2O_2$ in the following reaction steps:
 (1) Glucose+$GO_x$(FAD)→Glucorolactone+$GO_x$(FADH$_2$)
 (2) $GO_x$(FADH$_2$)+$O_2$→$GO_x$(FAD)+$H_2O_2$ The product $H_2O_2$ is then electrochemically oxidized on the working electrode surface of a probe of the biosensor, thereby generating an electrical current response signal to be measured. The blood glucose concentration can be correlated to the current response signal obtained from the oxidation of the $H_2O_2$, or to the electrochemical reduction of $O_2$, via the reversible reaction:

In order to accurately determine the blood glucose concentration from the obtained current response signal from the oxidation of $H_2O_2$, it is desirable for the working electrode to supply a stable constant voltage. In particular, if a stable voltage is produced by the working electrode, the electric current generated by this stable voltage can be accurately correlated to a blood glucose concentration after calibration of the sensor. Conversely, if the voltage generated by the working electrode is not stable and varies/drifts higher or lower than the expected voltage value, the electric current cannot be accurately used to determine a blood glucose value, because the voltage variations would produce unexpected changes in the current response signal. For example, if the voltage signal were to drop, a lower current response signal would be generated due to this voltage drop. If a sensor is not re-calibrated to account for the lower voltage being produced, the lower current response signal would be incorrectly detected as a lower glucose concentration of the user.

Conventionally, in order to maintain a stable working electrode voltage, a three-electrode biosensor is used. The three-electrode biosensor typically includes a working electrode, an auxiliary or "counter" electrode, and a reference electrode. When an adequate voltage difference is generated between the working and counter electrodes, the $H_2O_2$ is electrochemically oxidized on the working electrode. The voltage generated at the working electrode may be kept stable by determining the voltage difference between the working electrode and the reference electrode and then comparing this voltage difference to a predetermined value. If the voltage difference varies from the predetermined value, the voltage may be adjusted back to correspond to the predetermined value, thereby ensuring that a stable voltage value is maintained.

One problem with three electrode sensor probes is that the size of the implanted needle required to "house" a sensor having three electrodes is relatively large. Larger needle sizes increase patient discomfort and also result in a larger "foreign body response", thereby increasing biofouling on the sensor.

Accordingly, it is desirable to manufacture needles for glucose biosensor probes that decreases patient discomfort and reduces a foreign body response when the sensor probe is implanted into the patient.

Furthermore, other desirable features and characteristics will become apparent from the subsequent detailed description and the appended claims, taken in conjunction with the accompanying drawings and the foregoing technical field and background.

BRIEF SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

According to some embodiments, there is provided a method of operating a sensor for sensing glucose concentrations. The method includes applying, using a voltage controller, multiple voltage pulses to a working electrode of a two-electrode sensor probe. The method also includes measuring, using a current sensor, the current response to the applied multiple voltage pulses. The method also includes analyzing, using a processor, the measured current response. The method also includes calibrating, using a processor, the current sensor on the basis of the analyzed measured current response. The method also includes determining, using a processor, a glucose concentration value on the basis of the calibrated current sensor. The method also includes transmitting, using a transmitter, the determined glucose concentration value to a receiver.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The present inventors found that "larger" implantable sensor probes, such as sensor probes having an outer diameter over about 450 µm (i.e., requiring a needle size of over 26-gauge to implant the sensor probe in the patient), result in increased patient discomfort and an increased foreign body response from the patient. Furthermore, "larger" sensor probes usually incorporate three electrodes to achieve a higher signal to noise ratio of the measured analyte concentration signal, thereby increasing the accuracy of the obtained signal. The present inventors found that it is both difficult and expensive to manufacture a three-electrode sensor probe that can be implanted using a needle of 26-gauge or less.

As such, it was found that to efficiently achieve a miniaturization of the sensor to allow it to be implanted using a needle having a size of less than 26-gauge, a two-electrode sensor probe was required.

Figure 1:
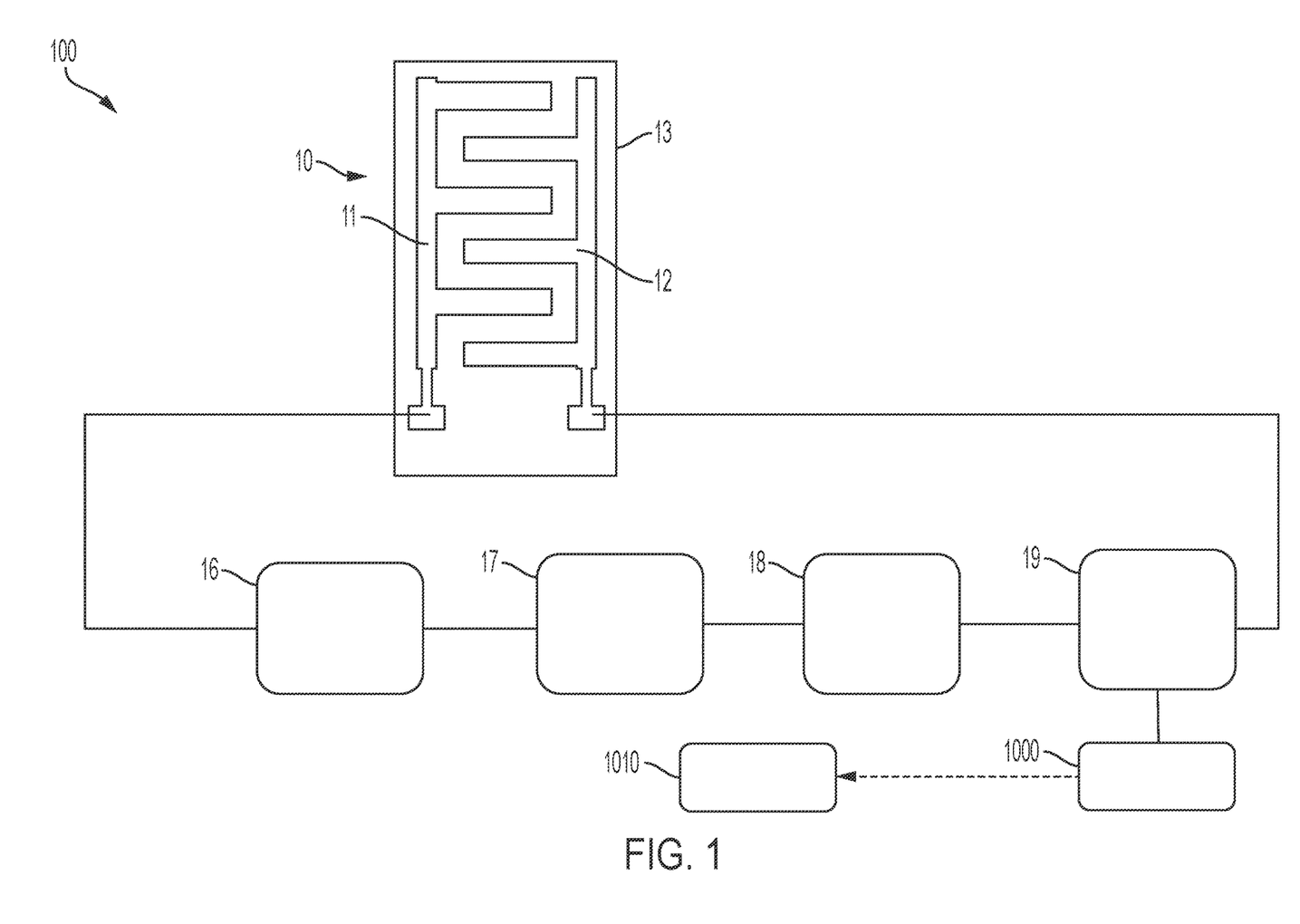
FIG. 1 is a top-down schematic of a two-sensor probe in accordance with exemplary embodiments.

FIG. 1 shows a top-down schematic of a two-electrode sensor probe 10 incorporated into a sensor 100 in accordance with exemplary embodiments. As can be seen in FIG. 1, the two-electrode probe 10 comprises two electrodes—a working electrode 11 and a counter electrode 12. The electrodes 11, 12 are formed over a base substrate 13. Although the working electrode and counter electrode are labelled as such in FIG. 1, it will be appreciated by the skilled person that the "role" of a particular electrode of the two-electrode probe 10 as either an anode or cathode will depend entirely on the potential that the electrode is biased at. For example, if the counter electrode 12 is biased at a higher voltage than the working electrode 11, the counter electrode 12 will then effectively become the working electrode, and vice versa.

As can be seen in FIG. 1, in exemplary embodiments, the two electrodes 11, 12 are inter-digitated. Inter-digitating the two electrodes allows for an increase in the surface area across which mediator species may transfer, thereby improving the signal to noise ratio of the obtained current response signal.

In exemplary embodiments, the two electrodes 11, 12 are formed using laser ablation techniques. In particular, the material used for the electrodes 11, 12 may be sputtered onto the substrate 13, and the shape of the electrodes are formed by laser-ablating the sputtered material. Since laser ablation techniques can typically achieve a very fine resolution, for example down to around 15 µm, the space between the electrodes 11, 12 may be minimized and the overall size of the sensor probe 10 may be reduced. In alternative exemplary embodiments, the material used for the electrodes 11, 12 may be electroplated onto the substrate 13 or may otherwise be deposited onto the substrate 13 by another deposition technique. In alternative exemplary embodiments, the shape of the electrodes 11, 12 may be formed by another formation technique, such as by chemical etching.

In exemplary embodiments, the material used to form the electrodes 11, 12 is platinum, and the material used to form the substrate 13 is polyester. In other exemplary embodiments, alternative bio-inert materials may be used for forming the electrodes 11, 12 and the substrate 13. For example, in an exemplary embodiment, the substrate 13 is polyethylene terephthalate (PET), which is a substantially chemically inert, high stiffness material.

Figure 2:
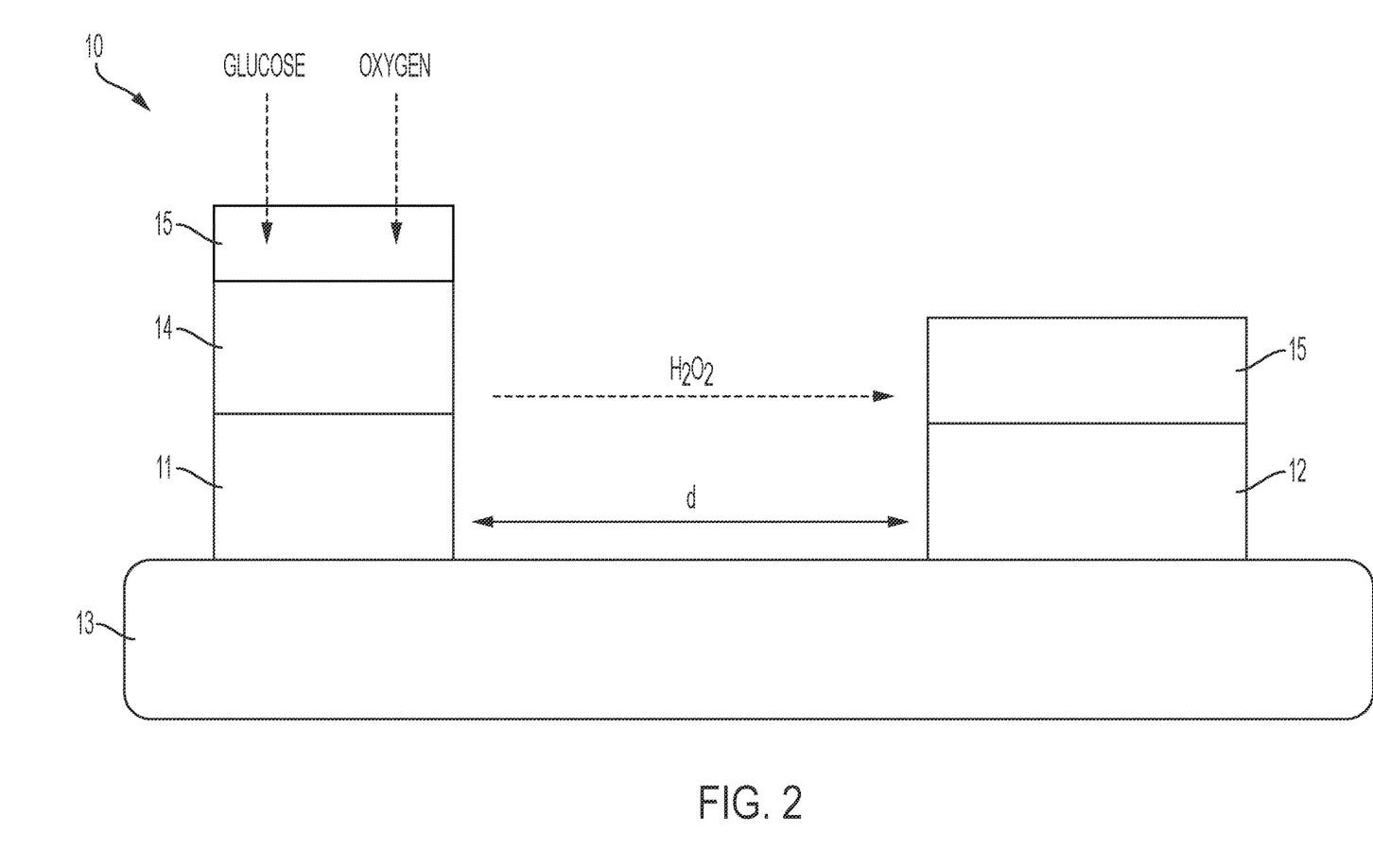
FIG. 2 is a side-view schematic of a two-sensor probe in accordance with exemplary embodiments.

FIG. 2 shows a side view of the two-electrode sensor probe 10. As can be seen in FIG. 2, the two-electrode probe 10 comprises a substrate 13 and two electrodes 11, 12 disposed over the substrate 13. The two electrodes 11, 12 are separated by a predetermined distance d.

As can also be seen in FIG. 2, the sensor probe 10 further comprises a catalytic layer 14 disposed over the working electrode 11. In exemplary embodiments, the catalytic layer 14 is a $GO_x$ layer configured to catalyze the reaction of glucose and oxygen at the working electrode 11. In exemplary embodiments, the catalytic layer 14 is deposited onto the working electrode 11 using photolithography techniques. In exemplary embodiments, the catalytic layer 14 may also be deposited over the counter electrode 12.

As can also be seen in FIG. 2, in exemplary embodiments the sensor probe 10 further comprises a flux-limiting membrane 15 disposed over each one of the electrodes 11, 12. The flux-limiting membrane 15 is configured to reduce the flux of glucose to the electrodes 11, 12. In particular, it is known that generally, the rate-limiting reactant in the glucose and oxygen reaction is oxygen, which is typically present at lower concentrations than glucose. As such, if there is an excess amount of glucose molecules at the working electrode 11, the sensed current may be artificially low because of a lack of oxygen available to react with the glucose present at the electrode. By using a flux-limiting membrane to limit the flux of glucose through this membrane to the working electrode 11, the likelihood of an artificially low current being sensed for this reason is reduced.

In exemplary embodiments, the flux-limiting membrane 15 is glucose limiting membrane, for example a polyurethane based polymer. In exemplary embodiments, the flux-limiting membrane 15 is disposed on top of the electrodes by a dip-coating technique.

Turning back to FIG. 1, it can be seen that the electrodes 11, 12 of the sensor probe 10 are operably connected to a power source 16, a voltage controller 17, a current sensor 18 and a processor module 19. The operable connections between these elements are only shown in a representative manner in FIG. 1. It will be appreciated that each one of the elements in this figure may have multiple connections to one or more of the other elements shown in this figure.

The voltage controller 17 is configured to supply, using the power source 16, a voltage signal to the electrodes 11, 12 in order stimulate the electrochemical reaction of glucose and oxygen to gluconic acid and $H_2O_2$ at the working electrode 11. The current sensor 18 is configured to sense the current response due to the $H_2O_2$ converting to oxygen, hydrogen ions and electrons, and then flowing from the working electrode 11 to the counter electrode 12. The current sensor 18 is configured to transmit this sensed current response signal to the processor module 19, and the processor module 19 is configured to subsequently analyze the current response in a manner which will be explained in more detail below. After analysis of the current response, the processor module 19 is configured to determine a glucose concentration value on the basis of the sensed current response. In exemplary embodiments, after determination of the glucose concentration value, the processor module 19 is configured to transmit the determined glucose concentration value to a transmitter 1000, which may (wirelessly or by another type of transmission method) transmit the determined glucose value to a remote receiver 1010 for viewing or action by a patient, or for actuating an insulin pump, etc.

As explained above, in three electrode systems a reference electrode is used to control the voltage applied to the working electrode. Since the presence of a reference electrode would increase the size of the sensor probe 10 of exemplary embodiments, the same manner of controlling the voltage applied to the working electrode 11 of the two-electrode sensor probe 10 cannot be used. As such, if a continuous voltage were to be applied to the working electrode 11, this continuous voltage would be liable to "drift", and the current response sensed by the current sensor 18 may not be representative of the actual glucose concentration proximate to the working electrode 10.

Furthermore, as with all biosensors, the sensor probe 10 is prone to biofouling. Biofouling as used herein refers to the situation where a biological membrane is deposited around the electrodes of the sensor 100 as a foreign body response, thereby inhibiting reactant flux to the electrodes 11, 12. Biofouling also causes sensor drift over time, since the diffusion rate of one or more reactants through the flux-limiting membrane 15 is decreased. Biofouling therefore may cause an artificial lack of a certain reactant around the electrodes 11, 12.

As such, it is necessary to calibrate the current response sensed by the current sensor 18 in order to ensure that accurate glucose concentration measurements are obtained.

Figure 3:
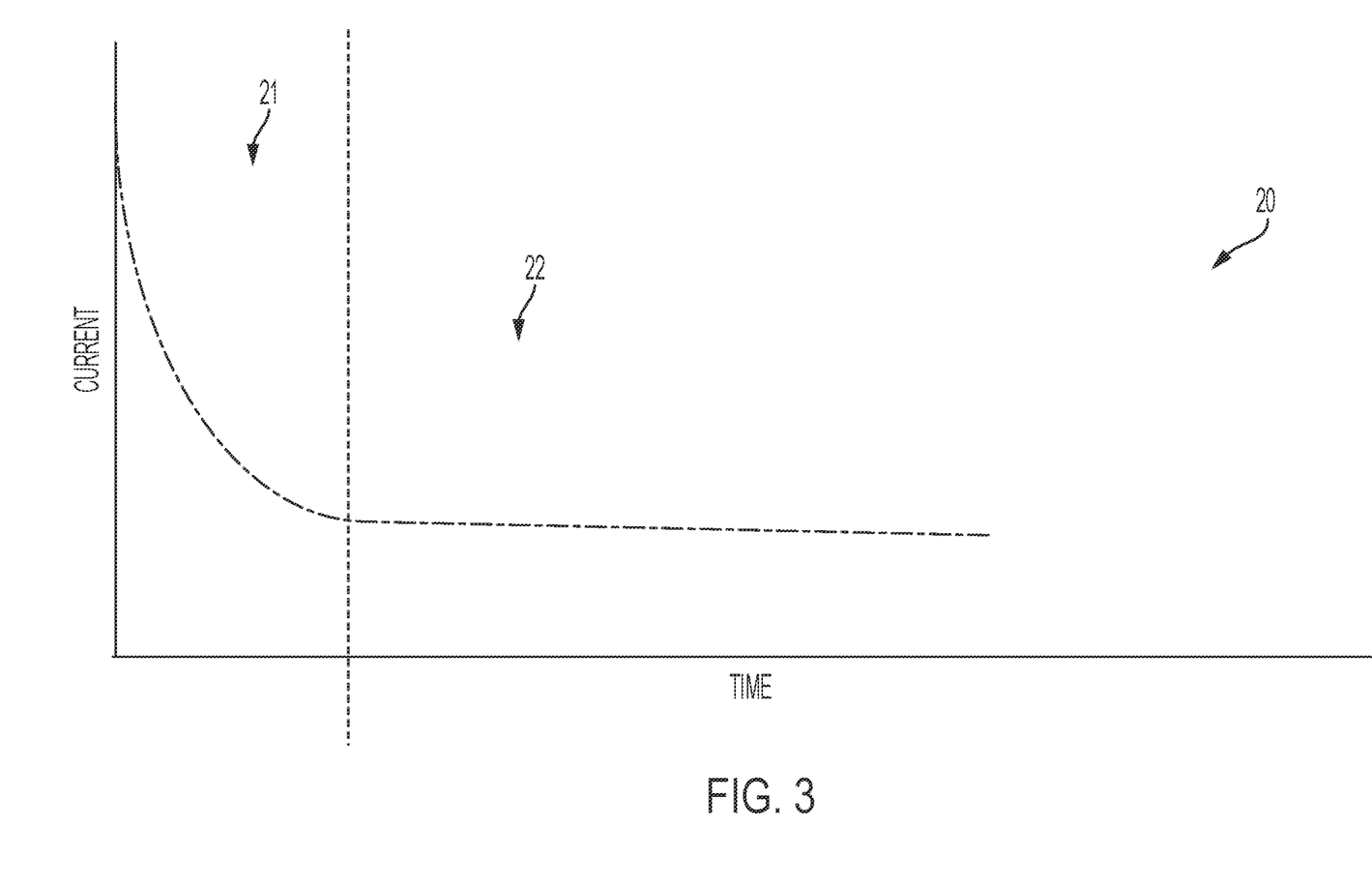
FIG. 3 is a schematic graph showing the initial "run-in" section of a current response.

The present inventors have found that signal calibration may be performed through analysis of a Cottrell profile of the sensed current response. A Cottrell profile results when the working electrode 11 of a biosensor is charged with a voltage. Initially, a high current is detected, which current is associated with this initial charging. Thereafter, the sensed current decreases, because the sensed current is dependent upon mediator species diffusing from the working electrode 11 to the counter electrode 12. The sensed current eventually declines to a plateau current, which is indicative of the recycling of mediator species between the two electrodes. An exemplary Cottrell curve 20 is shown in FIG. 3. As can be seen in FIG. 3, the curve 20 comprises two sections—a "run-in" section 21 where the sensed current decreases from an initially "high" sensed current in the same manner as described above, and a steady-state zone 22 where the sensed current is substantially unvarying over short time periods.

In the run-in section 21, the current decay can be modelled by the Cottrell equation:

$$I \propto \frac{1}{\sqrt{T}}$$

where I is current and T is time. As explained above, the current decrease in the run-in section 21 may be due to diffusional processes at the working electrode, but may also be due to capacitive charging and galvanic processes occurring between the working electrode and the counter electrode. It is to be noted that the run-in zone 21 lasts for a longer time in implanted sensors such as the sensor probe 10 as compared to traditional electrochemical sensors due to the movement of cells and biological species towards the sensor probe upon implantation of the sensor probe.

Figure 4:
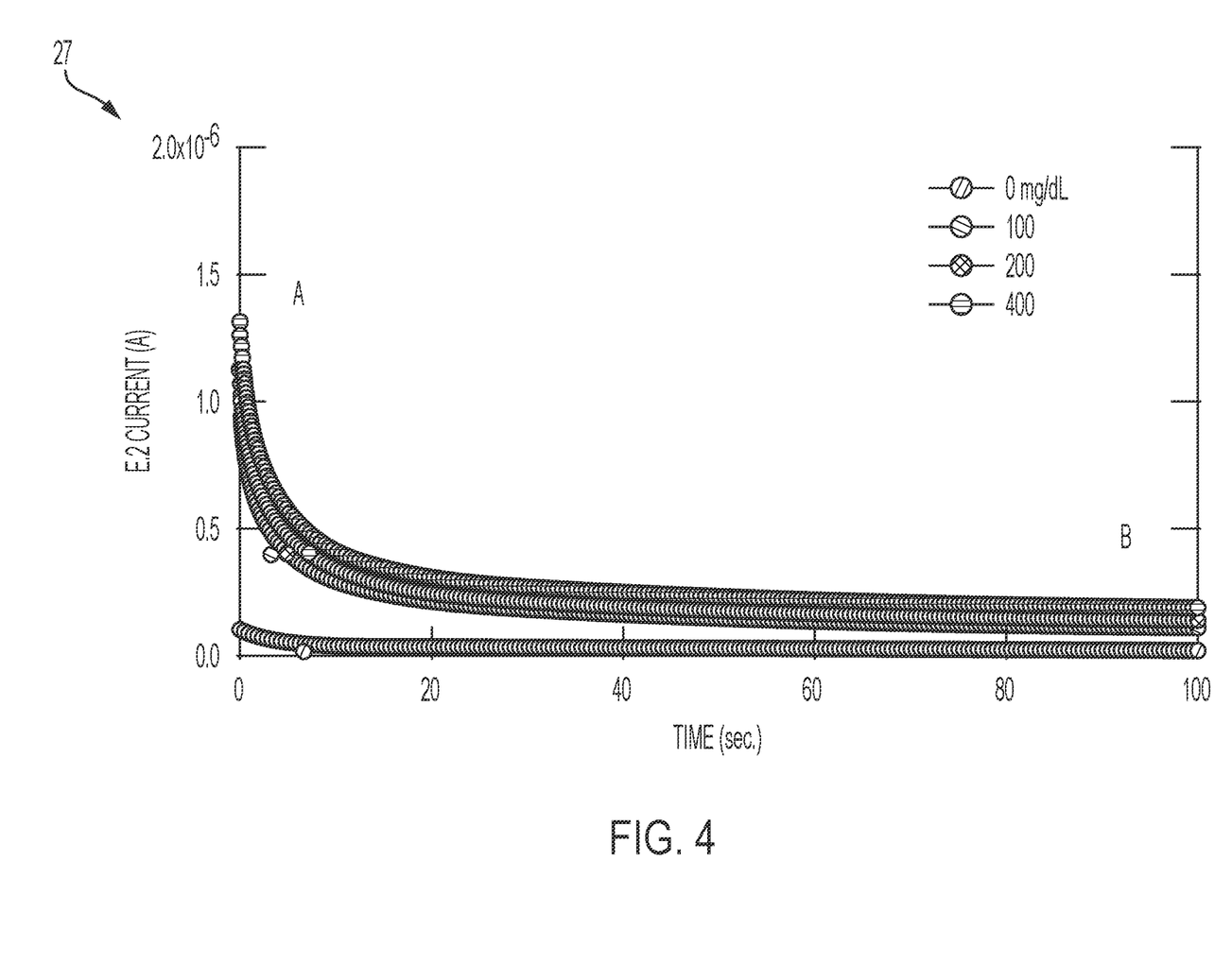
FIGS. 4 and 5 are graphs showing experimental current responses for varying glucose concentration values.
Figure 5:
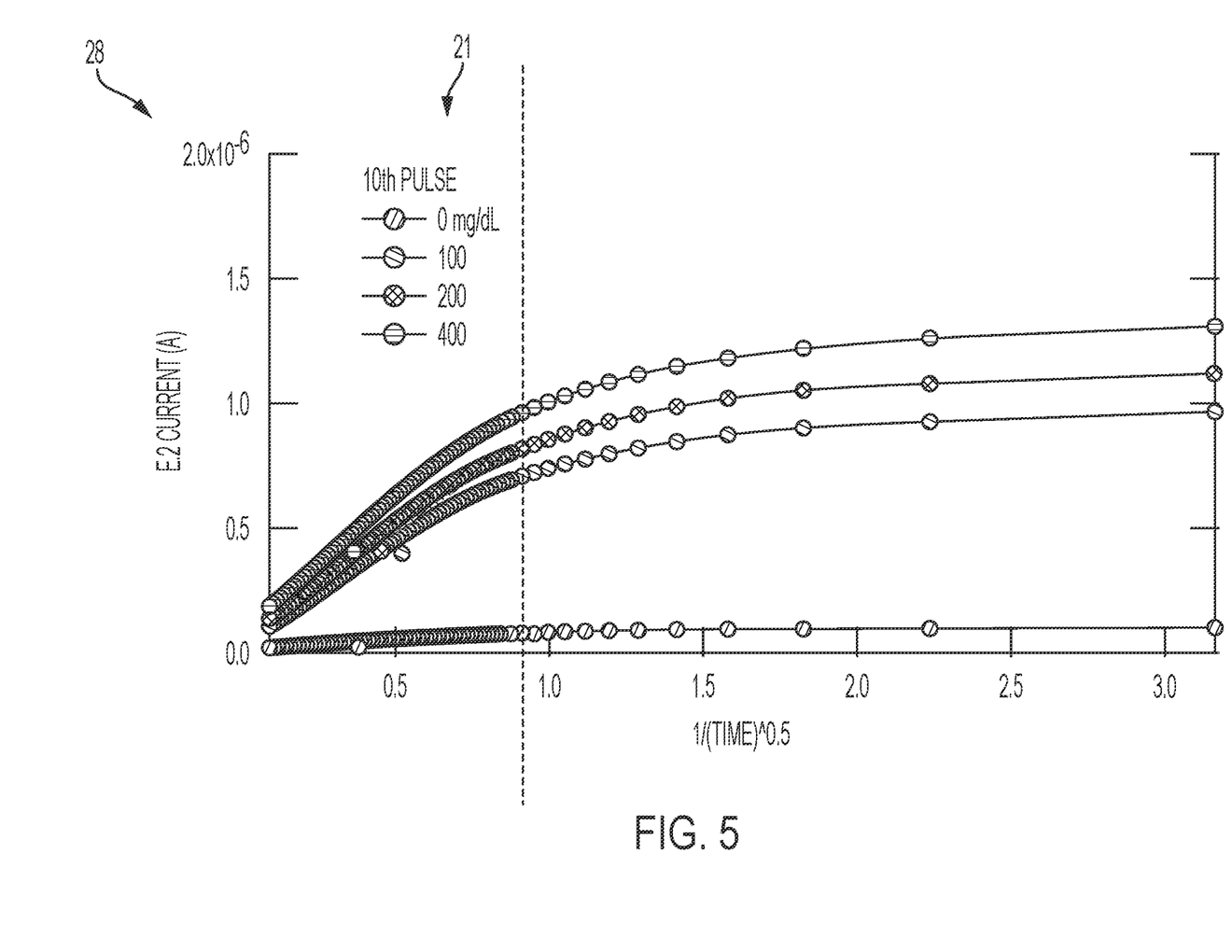

A Cottrell analysis can be performed on the current response in the run-in section 21 in order to determine the glucose concentration, as described in U.S. Pat. No. 5,243,516. A current vs. time plot and a Cottrell plot for different glucose concentrations are shown in FIG. 4 and FIG. 5, respectively. As can be seen in FIG. 4, a current vs. time plot 27 shows Cottrell curves derived experimentally for four different glucose concentrations: 0 mg/dL; 100 mg/dL; 200 mg/dL; and 400 mg/dL. FIG. 5, shows a different visualization plot 28 of the Cottrell curves for these four different glucose concentrations, where the sensed current is instead plotted against $$\frac{1}{\sqrt{T}}.$$

As can be seen in FIG. 5, it is possible to determine parameters associated with the sensed glucose values from the straight line corresponding to the run-in section 21 in this plot 28.

The present inventors have recognized that, instead of using the run-in sections 21 of the Cottrell profiles for determining the glucose concentration in the manner described in the prior art, the Cottrell profiles of the current response can be used for a different purpose, namely for calibrating the current sensor in order to mitigate for sensor drift. In particular, turning now to FIG. 6, the present inventors have found that by pulsing the working electrode 11 with a series of voltage pulses using the voltage controller 17, a quasi-Cottrell curve is obtained from the measured current.

Figure 6:
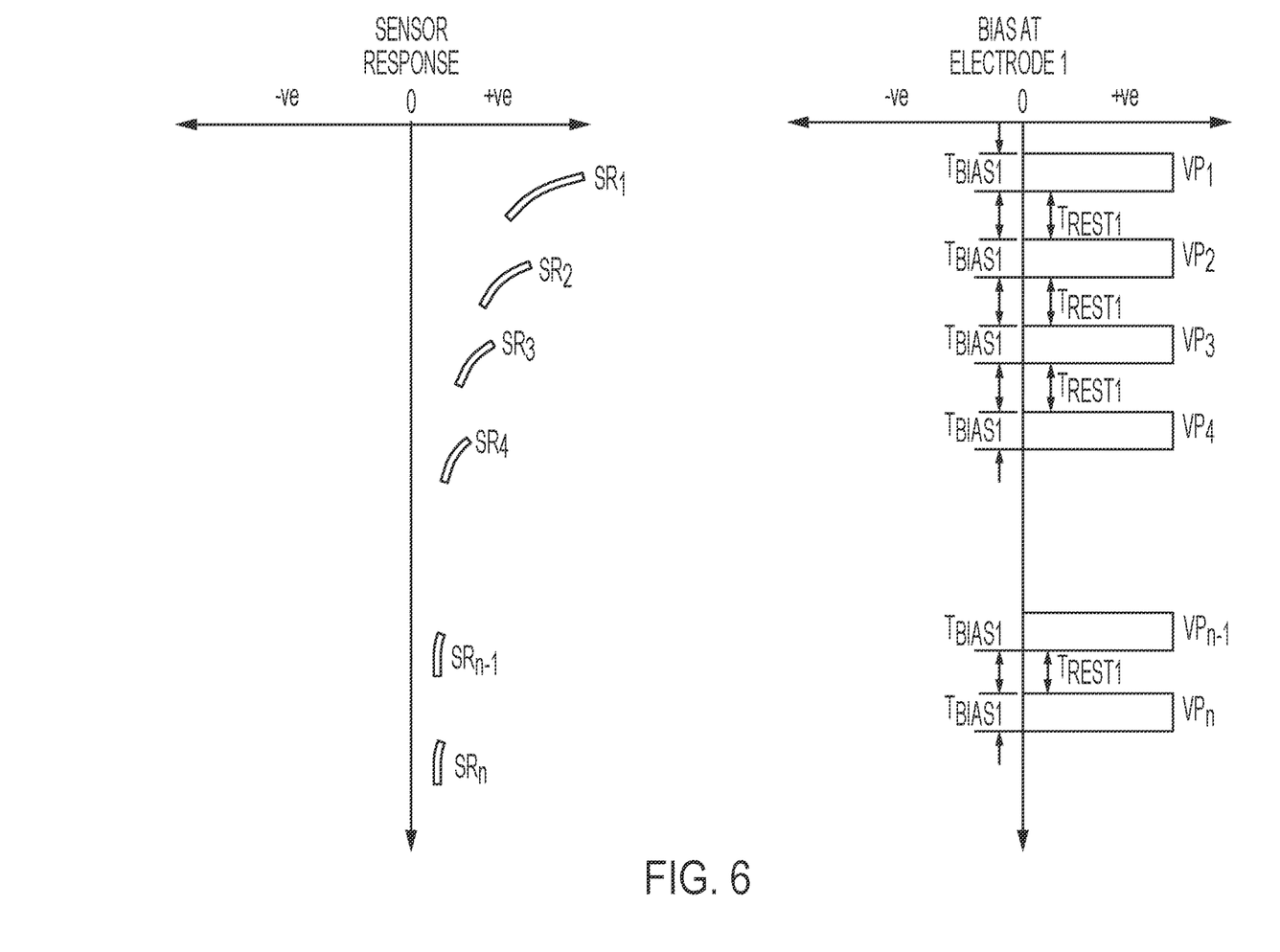
FIG. 6 shows the application of multiple voltage pulses in accordance with an exemplary embodiment.

As can be seen in FIG. 6, a series of voltage pulses (VP) $VP_1$ to $VP_n$ are applied to the working electrode, with each pulse being applied for a bias time $t_{bias1}$. The time between each pulse is kept constant at $t_{rest1}$. As each voltage pulse $VP_1$ to $VP_n$ is applied, a corresponding current sensor response $SR_1$ to $SR_n$ is measured. The shape of each individual sensor response curve $SR_1$ to $SR_n$ is unique, but the shape of the plurality of the sensor responses $SR_1$ to $SR_n$ forms the shape of a quasi-Cottrell curve.

By varying parameters associated with the series of voltage pulses (such as the time each pulse is applied for, the interval between each pulse, the magnitude of each pulse, and so on), it is possible to obtain different quasi-Cottrell profiles for the same glucose concentration. For example, the quasi-Cottrell profile obtained using pulses having a magnitude of around 0.5 V would be different to the quasi-Cottrell profile obtained using pulses having a magnitude of around 0.4 V.

The shapes of the different quasi-Cottrell profiles obtained by using different pulse parameters can be used for calibration purposes In particular, through a comparison of the shapes of different Cottrell profiles obtained using different pulse parameters to a series of pre-determined Cottrell profiles obtained for certain pulse parameters and certain glucose concentrations, the sensor can be automatically calibrated to correspond to the prior glucose concentration that has the same Cottrell profile. In particular, the rate of change of the sensor response may be compared, using a processor, to pre-determined rates of change for representative glucose concentrations, thereby allowing for calibration even when the exact value of applied voltage is unknown.

Such automatic calibration of the sensor allows for the accurate use of a two-electrode sensor, since this automatic calibration mitigates against voltage drift and other types of sensor drift, for example drift due to biofouling. In other words, the Cottrell profile can be used to determine the degree by which diffusional processes around the implant are affecting the current measurement. This degree to which the diffusional processes are affected can be measured and can then be used to automatically compensate for apparent changes in sensor sensitivity. Different patient disease states (such as Type 1 diabetes, which has a high glycemic variability over time or Type 2 diabetes, which has a lower glycemic variability over time) may also be taken into account through this comparison of the measured quasi-Cottrell profile to pre-determined Cottrell profiles.

In use, as explained above, the processor module 19 is configured to compare the shape of the determined Cottrell profile to a series of pre-determined Cottrell profiles. When a measured Cottrell profile corresponds to a pre-determined Cottrell profile, the processor module 19 is configured to calibrate the current sensor on the basis of the glucose concentration associated with the pre-determined Cottrell profile. Alternatively, the processor module 19 may calibrate the sensor on the basis of parameters calculated from the determined Cottrell profile without comparing the Cottrell profile to pre-determined Cottrell profiles, for example by determining the rate-of-change of current with respect to time during the run-in phase 21 and using this rate-of-change of current to calibrate the current sensor.

After calibration of the current sensor 18 using the Cottrell profile(s) obtained during the run-in section 21, an instantaneous current value is measured during the steady-state section 22 after the run-in section 21, and this current value is then used to determine glucose concentration values.

Figure 7:
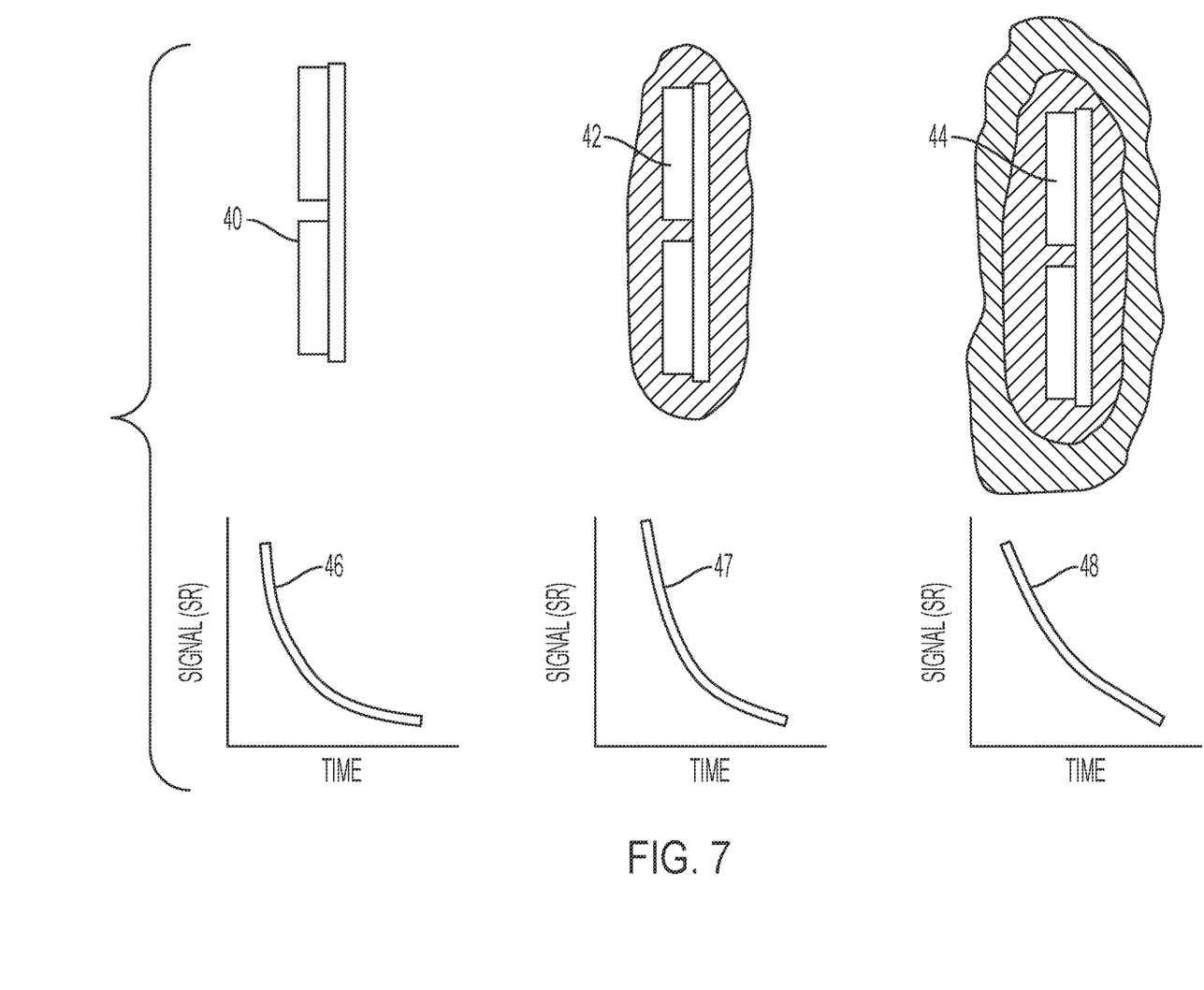
FIG. 7 shows different current responses experienced with respect to different levels of biofouling of a sensor.

Another example as to how the Cottrell profile may change due to an external factor is shown in FIG. 7. FIG. 7 shows respective "run-in" sections of representative Cottrell profiles 46, 47, 48 for a newly implanted sensor 40 having no biofouling; an implanted sensor 42 having a "minor" level of biofouling; and an implanted sensor 44 having a "heavy" degree of biofouling, respectively. As can be seen in FIG. 7, the rate of change of the current (also known as the "decay current") during the run-in phase of the Cottrell curve decreases as the level of biofouling increases. This is due to the electrochemical mediator transfer between electrodes taking longer due to the increased time needed for the mediators to diffuse through the membrane deposited around the sensor.

As explained above, by comparing parameters associated with the shape of the Cottrell curve (such as the rate-of-change of current in the run-in phase) to pre-determined Cottrell curves, a determination can be made as to the level of biofouling of the sensor, and the sensed current values can be calibrated correspondingly.

At least for the reasons given above, pulsing of the voltage signal to the working electrode 11 and the subsequent analysis of the Cottrell profile produced responsive to these voltage pulses allows for the processor module 19 to automatically calibrate the current sensor 18 as the implant environment evolves around the sensor. In particular, the pulsed voltages generates a current response in the form of a Cottrell profile which provides both a sensor signal for determining a glucose concentration value (in the "steady-state" section of the Cottrell profile) and also information about the reactant supply which can be used to calibrate the sensor (in the "run-in" section of the Cottrell profile).

In addition, pulsing of the voltage signal to the working electrode 11 also has additional benefit. In particular, by pulsing the voltage signal instead of applying a continuous bias to the working electrode, the power consumption of the sensor 10 can be reduced, and the service life of the power source 16 powering the sensor 10 can be extended. For example, by operating the sensor 10 in a pulsed mode, where the sensor 10 is powered for 1 second every 5 minutes, the sensor would be powered for a total of 4.8 minutes per day as compared to being powered for the 1,440 minutes per day required for continuous operation of the sensor. In other exemplary embodiments, the voltage controller 17 is configured to apply periodic blocks of voltage pulses for a limited time period, for example 100 seconds in every 500 seconds.

This reduction in power consumption is advantageous when attempting to reduce the overall size of the sensor 100 and associated components. In particular, with a reduced power consumption, a smaller power source 16 (for example a smaller battery) may be used to power the sensor, to thereby reduce the overall size and mass of the sensor 100, to require a smaller adhesive patch and to increase patient comfort.

To summarize the above, in use, the processor module 19 is configured to direct the voltage controller 17 to apply a series of voltage pulses to the working electrode 11. The current response to these voltage pulses is measured using the current sensor 18. The shape of the current response to the pulses is comparable to a Cottrell profile. The shape of the current response in the "run-in" section 21 of the Cottrell profile is then used for calibration of the current sensor 18 by the processor module 19. In other words, the processor module 19 is configured to alter the relationship between the sensed current and the correlated determined glucose concentration using information obtained from the shape of the "run-in" section of the current response. After calibration of the sensor on the basis of information obtained from the "run-in" section, instantaneous current measurements obtained in the "steady-state" phase are then used to determine glucose concentration values.

Figure 8:
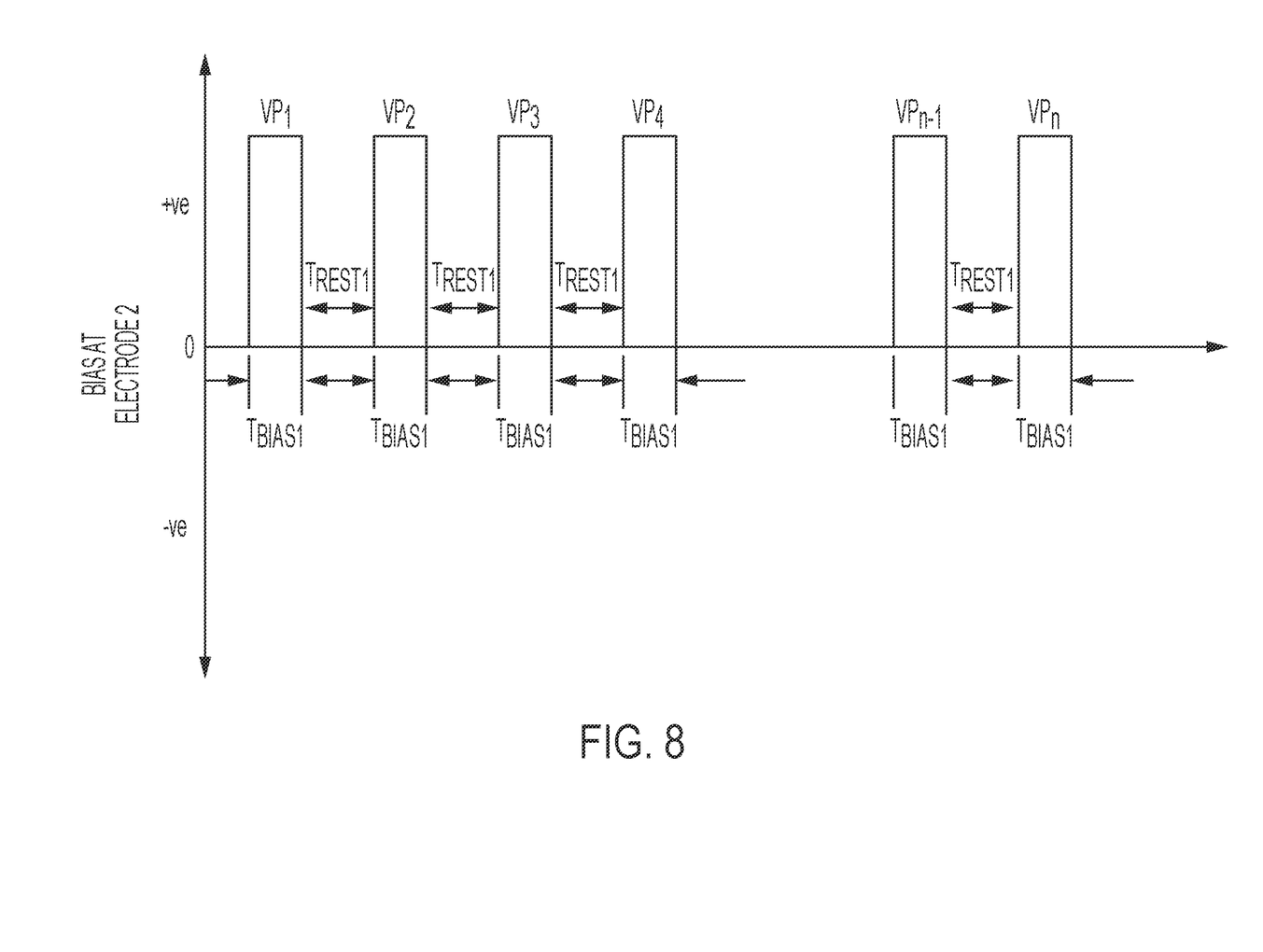
FIG. 8 shows regeneration voltage pulses in accordance with an exemplary embodiment.

As explained above, as the amount of oxygen proximate to the working electrode 11 decreases, the current sensed by the current sensor 18 may begin to artificially decrease and therefore cause a smaller glucose concentration to be determined than the actual glucose concentration present around the sensor. To counteract this sensor error caused by the oxygen deficiency, in exemplary embodiments the processor module 19 is configured to control the voltage controller to periodically "regenerate" the working electrode 11. More specifically, the processor module 19 is configured to cause the voltage controller 17 to apply a series of voltage pulses to the counter electrode 12. An exemplary series of regeneration pulses are shown in FIG. 8. The regeneration pulses have a predetermined magnitude, a predetermined pulse application time $t_{bias2}$ and a predetermined interval $t_{eq2}$ between subsequent pulses.

By applying a series of voltage pulses to the counter electrode 12, unutilized $H_2O_2$ is converted back to oxygen. The regenerated oxygen diffuses back to the working electrode 11 and alleviates the lack of oxygen around this electrode 11, thereby ensuring that a lack of oxygen at the working electrode 11 does not artificially skew the current sensed by the current sensor 18.

In an exemplary embodiment, the measurement and regeneration pulses are applied sequentially. In other words, a measurement pulse is applied to the working electrode to generate a current response signal, and then a regeneration pulse is applied to the counter electrode to regenerate the working electrode. In this manner, the likelihood that any current response signal is inaccurate due to an artificially low amount of oxygen is decreased, and the likelihood that the concentration measurement based on the current response signal is accurate is increased.

Figure 9:
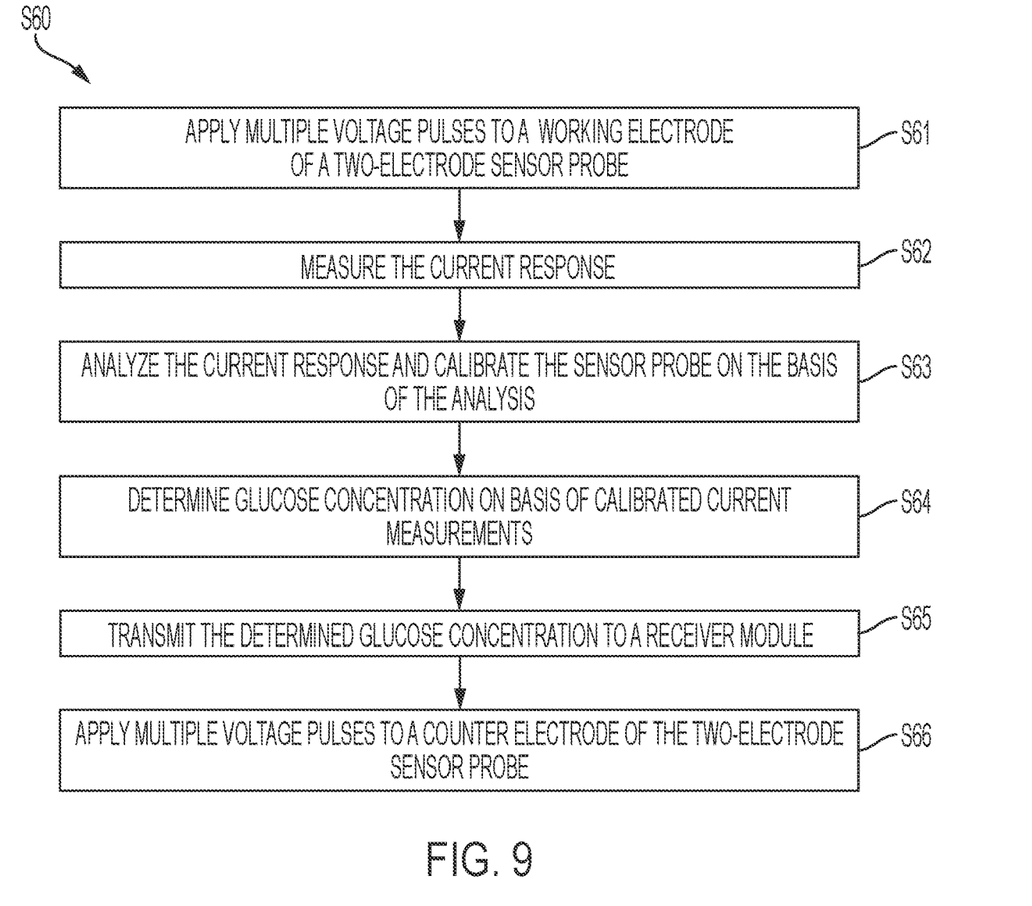
FIG. 9 shows a flowchart depicting a method in accordance with exemplary embodiments.

FIG. 9 shows a flowchart illustrating a method S60 of operating a sensor in accordance with exemplary embodiments. At step S61, multiple voltage pulses are applied, using a voltage controller and a power source, to a working electrode of a two-electrode sensor. The voltage pulses have a predetermined magnitude and period, and the interval between each one of the voltage pulses is also predetermined. The method then progresses to step S62.

At step S62, the current response is measured using a current sensor. The measured current response, which has the form of a Cottrell curve comprising a "run-in" section and a "steady-state" section, is transmitted to a processor module for analysis. The method then progresses to step S63.

At step S63, the current response is analyzed, using a processor module. Sensor calibration is performed, using the processor module, on the basis of a "run-in" portion of the measured current response. The sensor calibration is stored in a memory module associated with the processor module. The method then progresses to step S64.

At step S64, a glucose concentration is determined, using the processor module, on the basis of an instantaneous current measurement from the "steady-state" portion of the current response. The method then progresses to step S65.

At step S65, the determined glucose concentration is transmitted, using a transmitter module, to a receiver module in order for the determined glucose concentration to, for example, be viewed by a patient or to trigger the actuation of an insulin pump. The method then optionally progresses to step S66.

At optional step S66, multiple voltage pulses are applied, using the voltage controller and the power source, to a counter electrode of the two-electrode sensor in order to regenerate the working electrode. The multiple voltage pulses have a predetermined magnitude and period, and the interval between each one of the voltage pulses is also predetermined.

Figure 10:
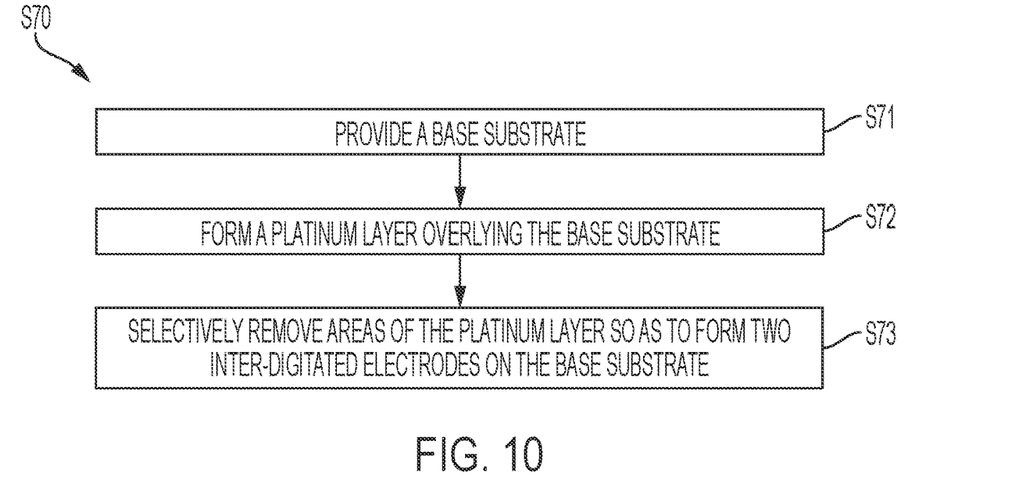
FIG. 10 shows a flowchart depicting a method in accordance with exemplary embodiments.

FIG. 10 shows a flowchart of a method S70 of forming a sensor probe for a biosensor in accordance with an exemplary embodiment. At step S71, a substrate is provided. The dimensions of the substrate are such that the substrate may be implanted using a needle of less than 26-gauge. In other words, the maximum dimensions of the substrate are such that the width of the substrate is less than 450 μm. In exemplary embodiments, the maximum dimensions of the substrate are such that the width of the substrate is less than 250 μm After provision of the base substrate, the method progresses to step S72.

At step S72, a platinum layer is formed overlying the base substrate. In exemplary embodiments, this platinum layer is formed by sputtering or electroplating platinum onto the base substrate. The method then progresses to step S73.

At step S73, areas of the platinum layer are selectively removed so as to form two inter-digitated electrodes. In exemplary embodiments, the selective removal of the platinum layer is performed by laser ablation. In alternative exemplary embodiments, the selective removal of the platinum layer is performed by etching.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

For the sake of brevity, conventional techniques related to biosensor probe manufacturing may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

The invention claimed is:

1. A method of operating a sensor for sensing glucose concentrations, comprising:
   applying, using a voltage controller, multiple voltage pulses to a working electrode of a two-electrode sensor probe;
   measuring, using a current sensor, a set of current responses corresponding to the applied multiple voltage pulses, wherein the set of current responses together form a quasi-Cottrell profile that approximates a portion of a Cottrell curve;
   analyzing, using a processor, the set of measured current responses;
   calibrating, using the processor, the current sensor on the basis of the analyzed set of measured current responses corresponding to the applied multiple voltage pulses, wherein calibrating the current sensor comprises comparing a characteristic of the quasi-Cottrell profile determined based on the analyzed set of measured current responses to sets of predetermined Cottrell profiles;

determining, using the processor, a glucose concentration value on the basis of the calibrated current sensor based on the comparison of the analyzed set of measured current responses to the sets of predetermined Cottrell profiles; and transmitting, using a transmitter, the determined glucose concentration value to a receiver.

2. The method of claim 1, further comprising applying multiple voltage pulses to a counter electrode of the two-electrode sensor probe to regenerate the sensor probe.

3. The method of claim 1, wherein the quasi-Cottrell profile has a run-in section and a steady-state section, and wherein calibrating the current sensor comprises calibrating the current sensor on the basis of an analysis of the run-in section.

4. The method of claim 3, wherein calibrating the current sensor comprises calibrating the current sensor on the basis of a measured rate of change of current with respect to time in the run-in section.

5. The method of claim 3, wherein analyzing the set of measured current responses comprises comparing the measured run-in section of the set of current responses with one or more run-in sections of pre-determined Cottrell profiles of the sets of predetermined Cottrell profiles.

6. The method of claim 3, wherein determining the glucose concentration value comprises determining the glucose concentration on the basis of an instantaneous current measurement measured by the current sensor in the steady-state section.

7. The method of claim 1, wherein applying the multiple voltage pulses comprises applying the multiple voltage pulses in periodic blocks, wherein a total application time of the periodic blocks is about one hundred seconds in every five hundred seconds.

8. The method of claim 1, wherein the sensor probe has a size to allow the sensor probe to be implantable by a needle of size 26-gauge or below.

9. The method of claim 1, wherein the multiple voltage pulses are separated by a constant rest time.

10. The method of claim 1, wherein the characteristic of the quasi-Cottrell profile is indicative of sensor drift.

11. The method of claim 1, wherein comparing the characteristic of the quasi-Cottrell profile to the sets of predetermined Cottrell profiles comprises selecting a predetermined Cottrell profile associated with a characteristic that matches the characteristic of the quasi-Cottrell profile.

12. The method of claim 11, wherein calibrating the current sensor comprises determining a known glucose concentration associated with the matching predetermined Cottrell profile.

* * * * *